US00PP26355P3

(12) United States Plant Patent
Korlipara

(10) Patent No.: US PP26,355 P3
(45) Date of Patent: Jan. 26, 2016

(54) ***BERGENIA* PLANT NAMED 'FLIRT'**

(50) Latin Name: ***Bergenia* hybrid**
Varietal Denomination: Flirt

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 122 days.

(21) Appl. No.: 14/120,310

(22) Filed: May 14, 2014

(65) Prior Publication Data

US 2015/0334906 P1 Nov. 19, 2015

(51) Int. Cl.
*A01H 5/00* (2006.01)

(52) U.S. Cl.
USPC ..... Plt./409

(58) Field of Classification Search
USPC ..... Plt./409
See application file for complete search history.

*Primary Examiner* — Annette Para
(74) *Attorney, Agent, or Firm* — Klarquist Sparkman, LLP

(57) ABSTRACT

A new and distinct *Bergenia* plant characterized by a vigorous, miniature habit, clean, shiny green late spring to summer foliage, numerous short inflorescences, large, deep pink flowers in a very showy spring display, and clean, shiny and almost black winter leaves.

2 Drawing Sheets

Botanical denomination: *Bergenia* hybrid.
Variety designation: 'Flirt'.

BACKGROUND OF THE INVENTION

The present invention relates to a new and distinct cultivar of *Bergenia* hybrid and given the cultivar name of 'Flirt'. *Bergenia* is in the family Saxifragaceae. The new cultivar originated from a planned breeding program to create small pot type *Bergenia*. The new cultivar was created from controlled crosses using proprietary parents. The exact parents were not recorded and are unknown.

SUMMARY OF THE INVENTION

This new *Bergenia* is unique in having:
1. a vigorous, miniature habit,
2. clean, shiny green late spring to summer foliage,
3. numerous short inflorescences,
4. large, deep pink flowers in a very showy spring display, and
5. clean, shiny and almost black winter leaves.

There are no similar *Bergenia* on the market.

Compared to *Bergenia* 'Pink Dragonfly', an unpatented small cultivar, the new cultivar has smaller leaves, more crowns and more flowering stems with shorter flower stalks.

This new cultivar has been reproduced only by asexual propagation (division and tissue culture). Each of the progeny exhibits identical characteristics to the original plant. Asexual propagation by tissue culture using standard micropropagation techniques with terminal shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a 9 month old *Bergenia* 'Flirt' in February in the trial gardens in Canby, Oreg.

FIG. 2 shows the same plant in bud and flower in early April.

DETAILED PLANT DESCRIPTION

Figure 3:
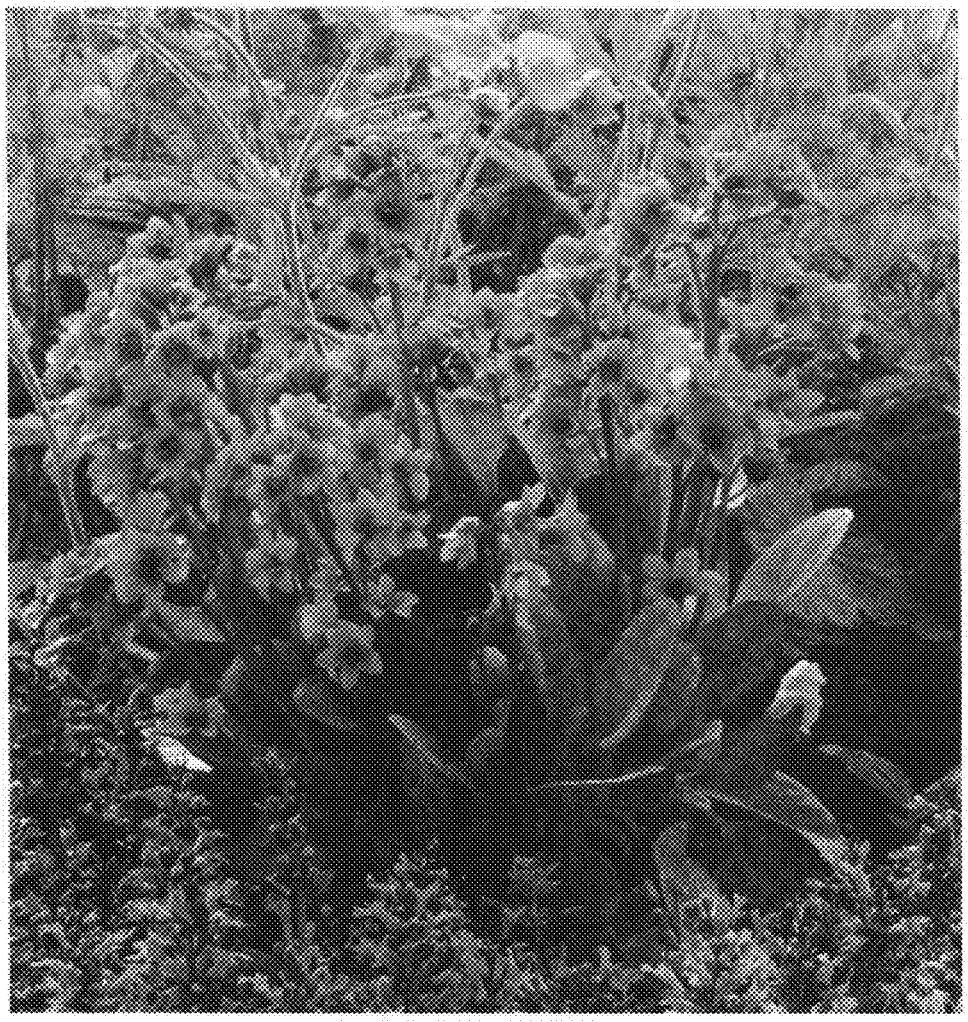
FIG. 3 shows the same plant in late April in the garden.

The following is a detailed description of the new *Bergenia* based on observations of nine-month-old specimens grown in the ground in full sun in the trial fields in late April in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:
- *Type.*—Herbaceous perennial.
- *Hardiness.*—USDA Zones 3 to 9.
- *Size.*—19 cm wide and 13 cm tall without flowers, 16 cm with flowers.
- *Form.*—Clumping.
- *# crowns.*—About 10, each with about 4 rosettes.
- *Vigor.*—Excellent.
- *Roots.*—Fibrous network, White 155A.

Leaf:
- *Arrangement.*—Rosette.
- *Number.*—About 5 per rosette.
- *Type.*—Simple.
- *Shape.*—Obovate.
- *Blade size.*—Grows to 7.5 cm long and 38 mm wide.
- *Margins.*—Dentate.
- *Apex.*—Acute.
- *Base.*—Cuneate.
- *Venation.*—Pinnate.
- *Surface texture.*—Glabrous on both surfaces.
- *Petiole description.*—Grows to 4.4 cm long and 6 mm wide, glabrous, base sheathing, sheath ligulate and spreading to 6 mm wide at base, Yellow Green 145B tinted Greyed Red 181A in sun in spring to Yellow Green 147B tinted Greyed Red 181A in winter.

*Color.*—Late spring and summer topside Green N137B with margin edged Greyed Purple 185A and with main vein and largest lateral veins Yellow Green 145B, bottom side Yellow Green 147C heavily tinted Greyed Purple 185A in sun and lower main veins 145C in shade; winter and early spring leaves topside Greyed Purple 187A with largest veins Greyed Purple 185B, bottom side Greyed Purple 187C.

Inflorescence:

*Type.*—Scapose cyme.

*Number of cymes.*—About 13.

*Number of flowers per scape.*—About 12.

*Size of inflorescence.*—Grows to 7 cm long and 5.5 cm wide.

*Peduncle.*—Grows to 13 cm tall and 5 mm wide, glabrous on bottom half to glandular near top, Yellow Green 147D in shade and Red Purple 185A in sun.

*Pedicel.*—Grows 4 mm to 8 mm long, 1.5 mm wide, glossy and glandular, Greyed Purple 187C.

Flower bud:

*Size.*—8 mm long and 5 mm wide.

*Shape.*—Ovoid.

*Surface.*—Glabrous.

*Color.*—Greyed Purple 187C.

Flower:

*Type.*—Bisexual.

*Size.*—11 mm long and 20 mm to 25 mm wide.

*Corolla description.*—11 mm long and 20 mm to 25 mm wide, bell-shaped, glabrous inside and out; petals, usually 8 in number, grow to 13 mm long and 9 mm wide, obovate, margin entire, tip obtuse, base attenuate, glabrous on both sides, topside Red Purple 64C darkening to 64A at base, bottom side 64D.

*Calyx description.*—10 mm long and 8 mm wide, campanulate, 5 lobes each 6 mm long and 3.8 mm wide, not overlapping, oblong, margin entire, tips obtuse, sparsely glandular outside, glabrous inside, color inside and outside Greyed Purple 183A.

*Pistil description.*—2 to 3, fused at base, Greyed Red 181B overall, each 6 mm long and 3 mm wide, ovary oval, 3 mm long and 3 mm wide; style 3 mm long and 2 mm wide, stigma 2 lobed, 3 mm wide.

*Stamen description.*—10 in number, 5 mm long, filaments 4.5 mm long, Red Purple 60C, anthers 0.5 mm long, Yellow White 158A; pollen White 155A.

*Bloom period.*—April in Canby, Oreg.

*Lastingness of bloom.*—Each flower lasts about a week.

*Fragrance.*—None.

Fruit: None seen.

Seed: None seen.

Pest and diseases: Pest and disease resistance are typical for this type of *Bergenia*. No known resistances.

I claim:

1. A new and distinct *Bergenia* plant as herein illustrated and described.

* * * * *

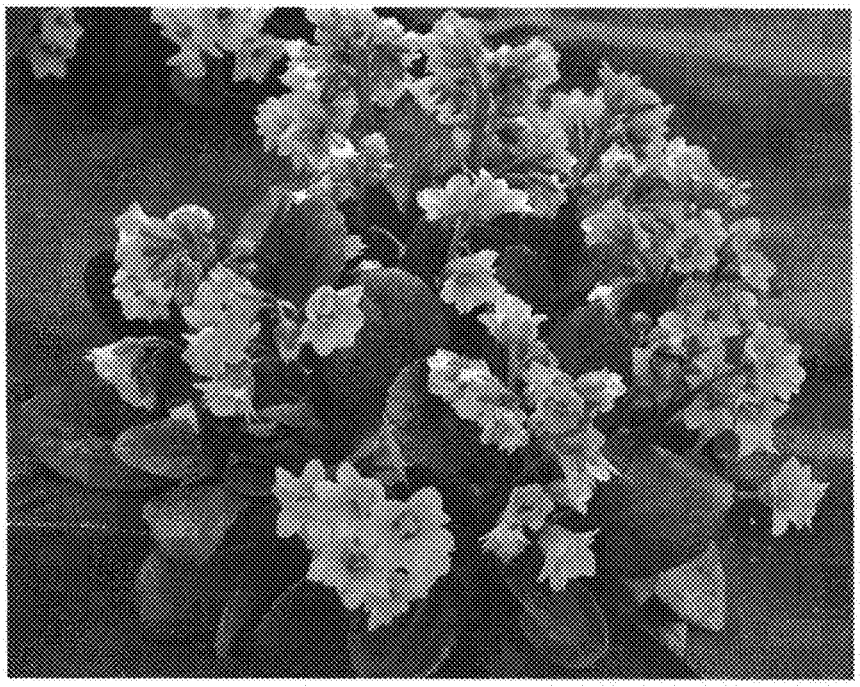

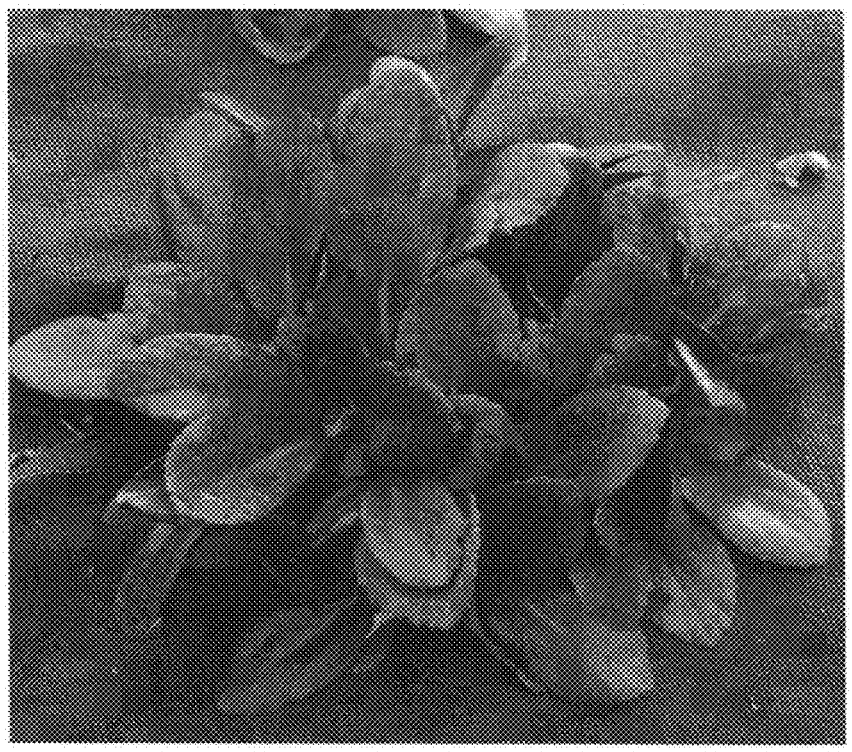
FIG. 1 above, FIG. 2 below